United States Patent [19]

Rabenau et al.

[11] Patent Number: 5,487,726
[45] Date of Patent: Jan. 30, 1996

[54] VACCINE APPLICATOR SYSTEM

[75] Inventors: Richard Rabenau, Birmingham; Fred E. Williams, Jr., Arab, both of Ala.

[73] Assignee: Ryder International Corporation, Arab, Ala.

[21] Appl. No.: 260,882

[22] Filed: Jun. 16, 1994

[51] Int. Cl.⁶ .................................................. A61B 17/20
[52] U.S. Cl. ............................ 604/46; 206/367; 206/438
[58] Field of Search ....................... 604/46, 47; 206/367, 206/438

[56] References Cited

U.S. PATENT DOCUMENTS

| | | | |
|---|---|---|---|
| 3,034,507 | 5/1962 | McConnell et al. | 604/46 |
| 3,221,739 | 12/1965 | Rosenthal | 604/47 |
| 3,675,766 | 7/1972 | Rosenthal | 604/47 |

OTHER PUBLICATIONS

*Dosage and Administration Instructions for Percutaneous Vaccine*, Organon Teknika, AKZO Corporation, Aug. 1990.

Primary Examiner—John D. Yasko
Attorney, Agent, or Firm—Trexler, Bushnell, Giangiorgi & Blackstone, Ltd.

[57] ABSTRACT

A percutaneous vaccine applicator system which includes a percutaneous vaccine applicator and a packaging assembly for housing the vaccine applicator. The percutaneous vaccine applicator includes a handle and spiked portion attached to the handle. A plurality of spikes project from the spiked portion for puncturing the skin of a patient to deliver a percutaneous vaccine. The packaging assembly includes a hollow container and a removable cover attached to the container. The hollow container defines a cavity being sized and dimensioned for receiving the vaccine applicator. The container has structures for positively receiving and retaining an applicator placed therein.

10 Claims, 3 Drawing Sheets

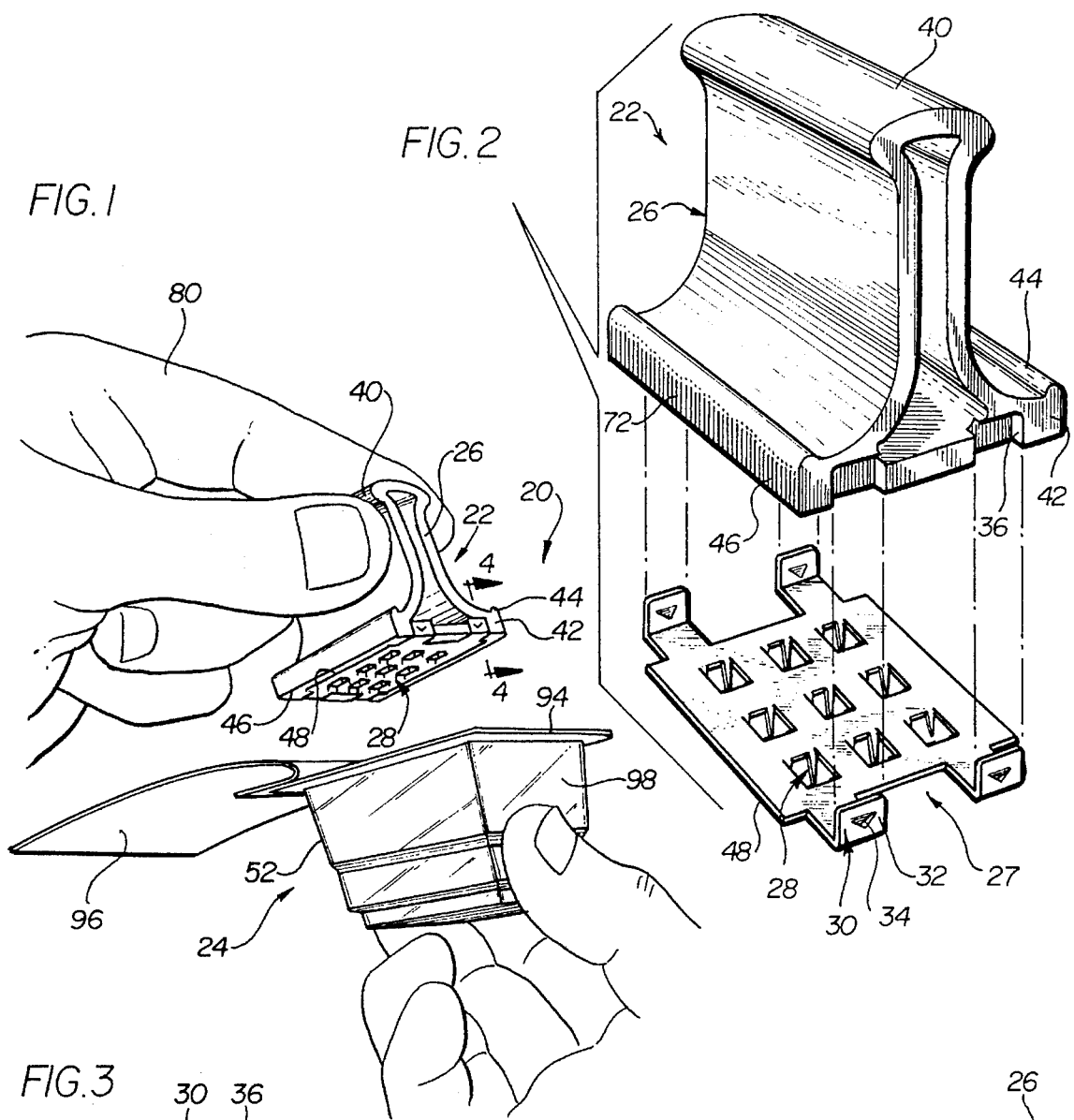
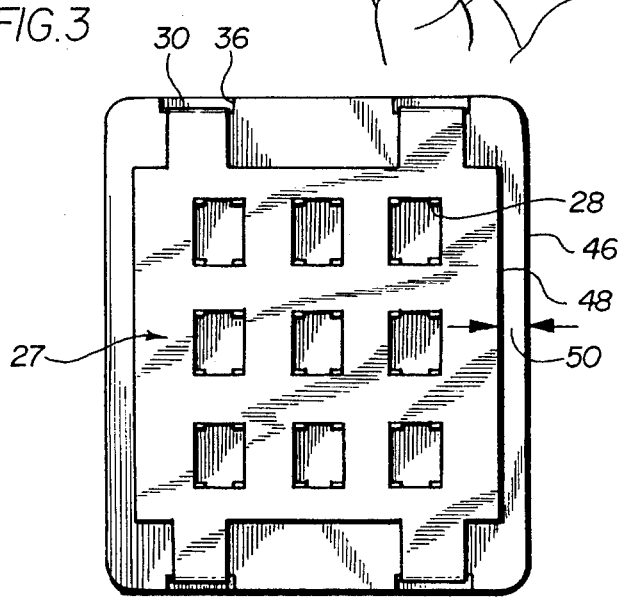
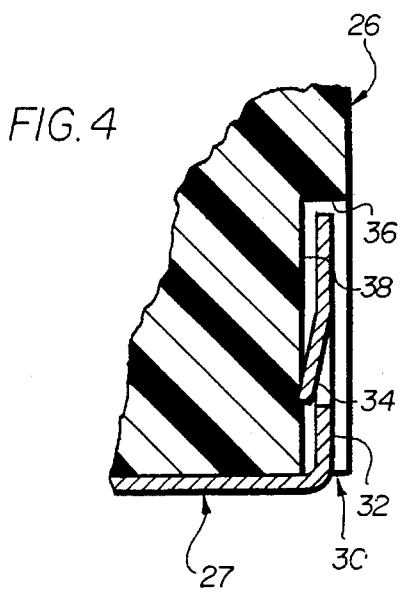

:::: 5,487,726

VACCINE APPLICATOR SYSTEM

BACKGROUND

The present invention relates to percutaneous vaccine applicator systems and more specifically a percutaneous vaccine applicator system which minimizes the risk of cross contamination by way of the applicator between the person administering the vaccine and the recipient of the vaccine.

A variety of vaccines are administered by percutaneous inoculation. A percutaneous inoculation requires piercing the surface of a patient's skin to deliver the vaccine immediately under the surface of the skin. For example, prior art procedures start by swabbing or wiping a dose of vaccine over a selected area of a patient's skin. Often the vaccine is swabbed on a small area of the patient's arm approximating the size and shape of the vaccine applicator. The vaccine applicator includes a plurality of spikes which are used to puncture a patient's skin and drive the vaccine underneath the skin. The applicator is positioned over the vaccine swabbed area and a force is applied to the applicator so that the spikes penetrate the skin surface. A portion of vaccine is delivered below the skin surface by the action of the spikes penetrating the skin. The applicator is lifted from the patient's skin and the vaccine in the swabbed area is wiped into the punctures created by the spikes to assure maximum delivery of vaccine.

Such a vaccine delivery system is utilized to inoculate people with tuberculosis vaccine. Without going into detail regarding tuberculosis or specific vaccines, it is preferable to deliver certain types of tuberculosis vaccine percutaneously. Other vaccines may also be delivered in this manner.

Tuberculosis infections have been increasing throughout the world and as such it is extremely important to increase vaccination efforts to prevent or minimize the spread of tuberculosis. While tuberculosis is a highly communicable disease which primarily affects the lung and may be terminal, vaccination against tuberculosis is highly effective.

As will be discussed hereinbelow, prior art percutaneous vaccination applicator systems are difficult to use, create blood contamination hazards for technicians, patients and waste handlers, and disposal problems. As such it would be highly desirable to provide a percutaneous vaccine applicator system which overcomes the prior art problems.

Prior art applicator systems create many problems in the percutaneous application of vaccines. The prior system includes a very thin, wafer-like stainless steel plate with numerous spikes protruding from one of the surfaces. The thin wafer-like plate can be very small measuring ⅞ inches by 1⅛ inches. This wafer-like plate is provided in sterilized flexible material pouch which is subject to being punctured by the spikes on the plate.

The packaging for the spiked plates provides a potential for contamination. First, the plate may be contaminated by puncturing the pouch thereby breaching the sterility of the pouch. Secondly, if the pouch is pierced, a person handling the pouch may contaminate the tips of the spikes if they are punctured or if they in any way handle the plate. Additionally, the tips of the spikes may become dulled by piercing the pouch material or bumping against other surfaces after having pierced the pouch material. Dulled spiked surfaces make administration of the vaccine more difficult and more painful for the patient.

Employing the vaccination procedures described hereinabove, a plate is removed from a pouch and picked up using a magnetic handle. The magnetic handle is used to position the plate over a vaccine swabbed area on a patient's arm and drive the spikes through the vaccine and into the patient's arm. Once the spikes are buried in the skin, the handle is rocked forward and backward several times to assure that each spike has punctured the skin surface.

Next, the magnetic handle is slid to one side to disengage the handle from the plate. In a successful procedure, the spikes remain buried in the skin after the magnetic handle is removed from the plate. This step of the operation provides yet more opportunities for contamination. First, while the spiked plate is a disposable component of the vaccination system, the handle is intended to be reused. Since the handle may directly contact the vaccine and/or body fluids such as blood which may well up into the punctures created by the spikes, it is almost certain that the handle will become contaminated. Further, because the handle is a reusable item, there is the possibility that the handle may not be completely or properly sterilized and thus may contaminate other technicians or patients.

This step introduces further discomfort for the patient since the embedded spike are twisted while the handle is removed. The plate then must be lifted from the patient's arm for use in wiping the vaccine into the punctures created by the spikes. In order to lift the plate from the patient's arm one end is usually depressed into the flesh to get the opposite end to lift from the arm; causing further patient discomfort.

Proceeding with the prior art vaccination system operation, the plate is removed by the operator and one edge of the plate is used to spread vaccine into the puncture sites. Herein lies yet additional possibilities for contamination of the technician and patient. The technician may be contaminated by handling the spiked plate while removing the plate from the patient's arm and while wiping vaccine into the punctures. If a spike pierces the technician, the technician may become infected by any diseases carried by the patient. Further, after the technician is punctured, the technician may infect the patient with any diseases he may be carrying. It is apparent that the prior art provides numerous opportunities for cross contamination between technician and patient.

As an additional matter, the plates must be disposed of after completing the vaccination procedure. The packaging for the plates is a flexible material pouch. Since the pouch presents the risk of contamination before use, the pouch also presents the risk of contamination by a used spike plate. This risk of contamination goes beyond the technician and patient such that any other individual handling the very sharp multi-spiked vaccine and fluid coated medical waste, such as waste handlers, risks contamination.

While the risk of contamination by minor diseases and tuberculosis is highly undesirable, this risk is additionally alarming due to the current spread of AIDS. In view of the spread of AIDS, most medical facilities are taking additional measures to prevent cross contamination of bodily fluids. As such, it would be highly desirable to overcome the problems with the prior art discussed hereinabove.

OBJECTS AND SUMMARY

A general object of the present invention is to provide a vaccine applicator system which reduces the risk of accidental contamination by an applicator used in the system.

Another object of the present invention is to provide a percutaneous vaccine applicator which is fully disposable and protects a technician and patient against contamination.

Yet another object of the present invention is to provide a packaging assembly for a vaccine applicator system to prevent contamination to the applicator as well as the technician and patient.

Briefly, and in accordance with the foregoing, the present invention envisions a percutaneous vaccine applicator system which includes a percutaneous vaccine applicator and a packaging assembly for housing the vaccine applicator. The percutaneous vaccine applicator includes a handle and spiked portion attached to the handle. A plurality of spikes project from the spiked portion for puncturing the skin of a patient to deliver a percutaneous vaccine. The packaging assembly includes a hollow container and a removable cover attached to the container. The hollow container defines a cavity being sized and dimensioned for receiving the vaccine applicator. The container has structures for positively receiving and retaining an applicator placed therein.

BRIEF DESCRIPTION OF THE DRAWINGS

The organization and manner of the structure and operation of the invention, together with further objects and advantages thereof, may be understood by reference to the following description taken in connection with the accompanying drawings, wherein like reference numerals identify like elements, and in which:

FIG. 1 is an perspective view of a vaccine applicator system of the present invention showing a vaccine applicator removed from a packaging assembly for the applicator;

FIG. 2 is an exploded perspective view of the applicator showing a spiked portion exploded from a base of an applicator handle;

FIG. 3 is a bottom plan view of the applicator showing the spiked portion attached to the base of the handle;

FIG. 4 is an enlarged partial fragmentary cross-sectional view taken along line 4—4 in FIG. 1 showing attachment of the spiked portion to the base;

DETAILED DESCRIPTION OF THE PREFERRED EMBODIMENT

Figure 5:
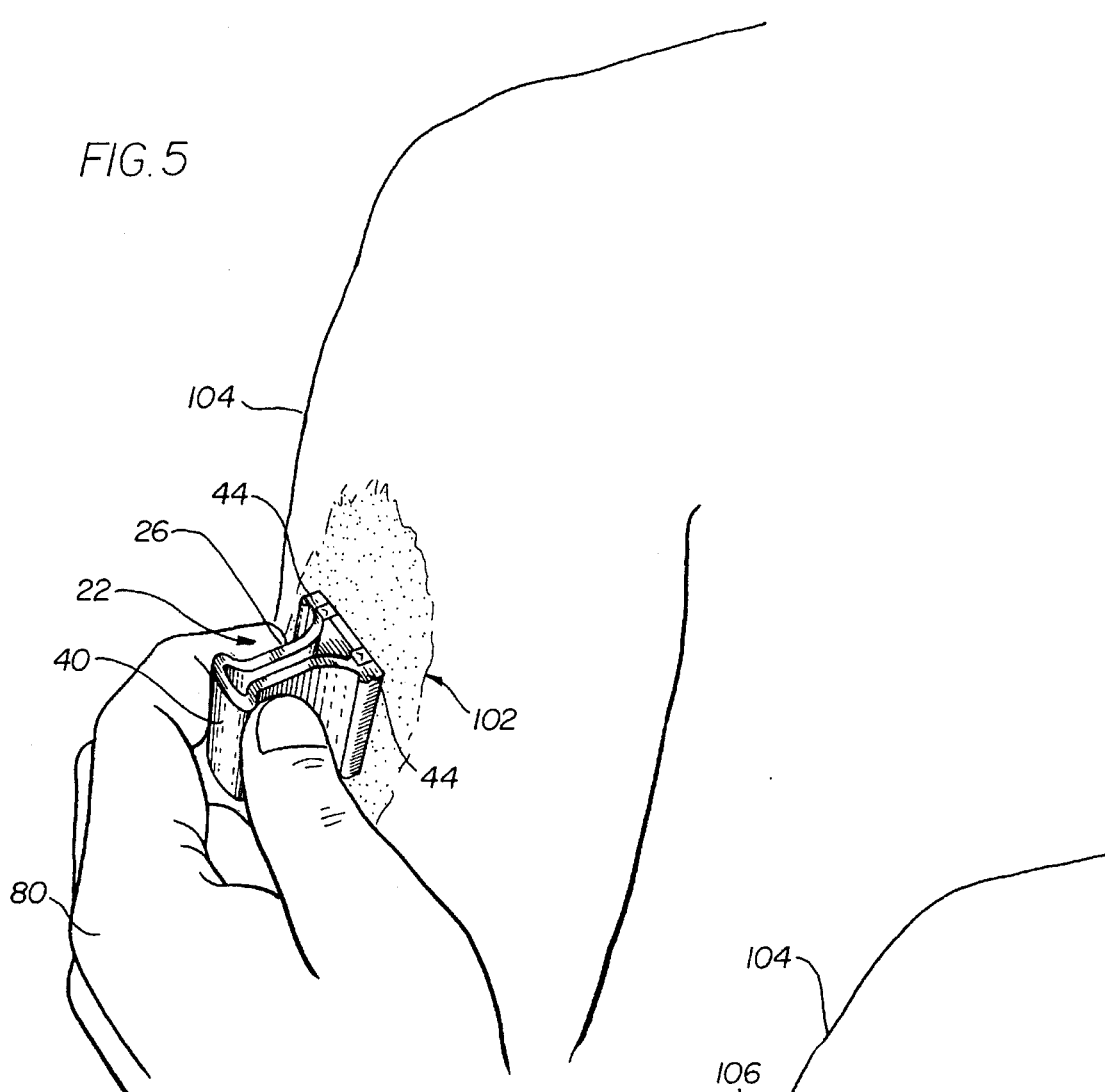
FIG. 5 is a partial fragmentary view showing a vaccine applicator of the present invention positioned over an inoculation site on a patient's arm which has been prepared with a vaccination substance.

While the invention may be susceptible to embodiment in different forms, there is shown in the drawings, and herein will be described in detail, an embodiment with the understanding that the present description is to be considered an exemplification of the principles of the invention and is not intended to limit the invention to that as illustrated and described herein.

Figure 7:
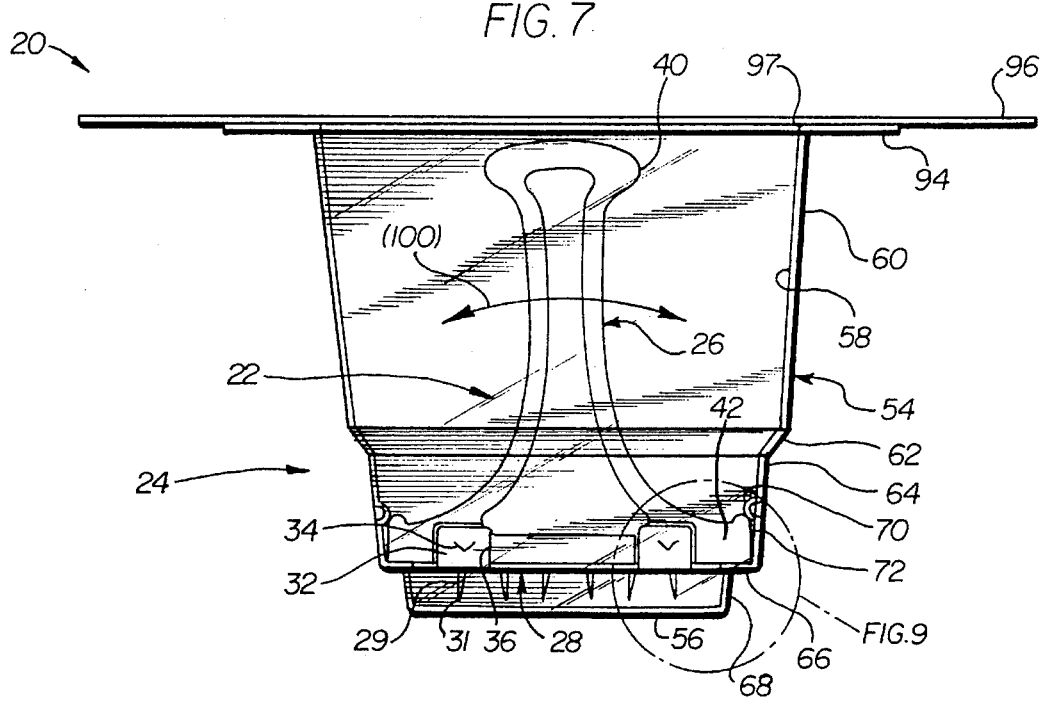
FIG. 7 is a front elevational view of the vaccine applicator system of the present invention showing the vaccine applicator positioned in the packaging assembly.
Figure 8:
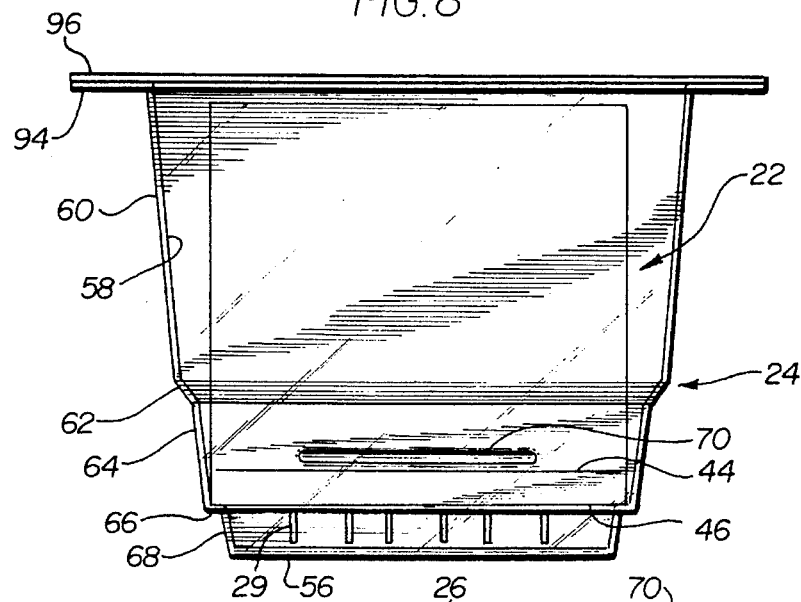
FIG. 8 is a side elevational view of the vaccine applicator system as shown in FIG. 7.

FIG. 1 shows the percutaneous vaccine applicator system 20 of the present invention. The applicator system 20 includes the applicator 22 and packaging assembly 24. With reference to FIG. 2, the applicator 22 includes a handle portion 26 and substrate member 27 defining a spiked portion 28, which substrate member 27 is attachable to the handle portion 26. The spike portion 28 includes a plurality of tines or spikes 29 have precision formed and/or sharpened tips 31. With reference to FIGS. 7 and 8, the applicator 22 is retained inside the packaging assembly 24 before and after use.

Turning to FIGS. 2–4, the substrate member 27 with its spiked portion 28 is attached to the handle 26 by the attachment means 30. The attachment means 30 include attachment tabs 32 extending from the periphery of the substrate member 27, said tabs having barbs 34 formed on an upstanding portion thereof. The handle 26 is provided with a recess 36 formed and cooperatively positioned for engagement with the attachment tabs 32. When the substrate 27 with its spiked portion 28 is mounted to the handle 26, the plate is positioned so that the attachment tabs 32 engage the corresponding recesses 36 whereby (see FIG. 4) the barbs 34 engage or lodge against an inside surface 38 of the recess 36. When attached, the spiked portion 28 is not easily dislodged from the handle 26.

The handle 26 includes a grip portion 40 and a base portion 42. The grip and base 40, 42 may be integrally formed as a single piece extrusion or molding with the recesses 36 formed therein. Also formed on the base 42 are guard sections 44 and a wiping edge 46. With reference to FIG. 3, an edge 48 of the spiked portion 28 extending parallel to the wiping edge 46 is spaced away from the wiping edge a dimension (as indicated by dimension reference numeral 50). The dimension (50) is provided between the edge 48 of the spiked portion and the wiping edge 46 so that when the wiping portion is employed to redistribute vaccine, as will be discussed in further detail hereinbelow, the edge 48 of the spiked portion 28 of substrate 27 does not interfere with the wiping operation.

The applicator system 20 of the present invention is designed to maintain the vaccine applicator 22 in sterile state within the packaging assembly 24 prior to use and to safely dispose of the applicator 22 in the packaging assembly 24 after use. Additionally, the packaging 24 helps to prevent the tips 31 the spikes 29 from being dulled or becoming bent. In this regard, the packing assembly 24 maintains a sterile environment prior to use and provides a puncture resistant and puncture protecting container for disposable of the applicator 22. The packaging 24 retains the tips 31 of the spikes 29 spaced away from surfaces to prevent puncturing and potentially dulling or bending contact with the spike tips.

The packaging assembly 24 includes a hollow container 52 which has walls 54 and a base panel 56 defining a cavity 58. The walls 54 include an upper wall portion 60, a connected step portion 62, an intermediate wall portion 64, a connected ledge 66 and a lower wall portions 68. The component proportions 60, 62, 64, 66, 68 of the walls 54 are integrally formed with the base portion 56.

Figure 9:
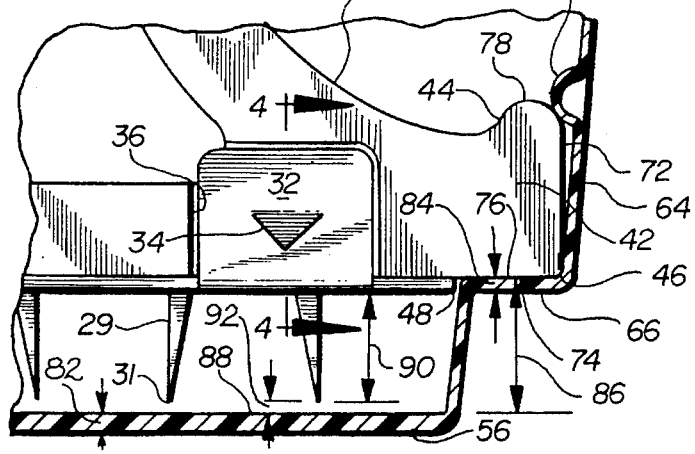
FIG. 9 is an enlarged, partial fragmentary, cross-sectional view shown in focus area "FIG. 9" in FIG. 7 showing engagement of the applicator in the container of the packaging assembly.

An inwardly protruding rib 70 is formed in the intermediate wall 64 spaced along the intermediate wall away from the ledge 66 a sufficient distance to capture an outside edge 72 of the base 42. The rib 70 is an elongated protrusion which extends generally parallel to the wiping edge 46 and the guard section 44 of the handle 26. As shown in FIGS. 7–9, a bottom surface 74 of the base 42 abuts an upper surface 76 of the ledge 66. An upper edge 78 of the guard section 44 abuts the ribs 70 in an interference fit sufficient to prevent accidental disengagement of the applicator 22 from the container 52. The ribs 70 positioned on opposite sides of the base 42 provide symmetric engagement of the applicator 22 in the container 52.

In the sterile state prior to use, the ribs 70 retain the applicator in the container 52 to prevent movement of the applicator 22 and thus preventing potential breach of the sterile environment inside the container, for example as a result of a tip 31 of a spike 29 puncturing the base panel 56. After use, the applicator 22 is returned to the cavity 58 of the container 52 and the base 42 is engaged with the ribs 70 to provide safe disposal and/or contact with the spiked portion 28.

Figure 6:
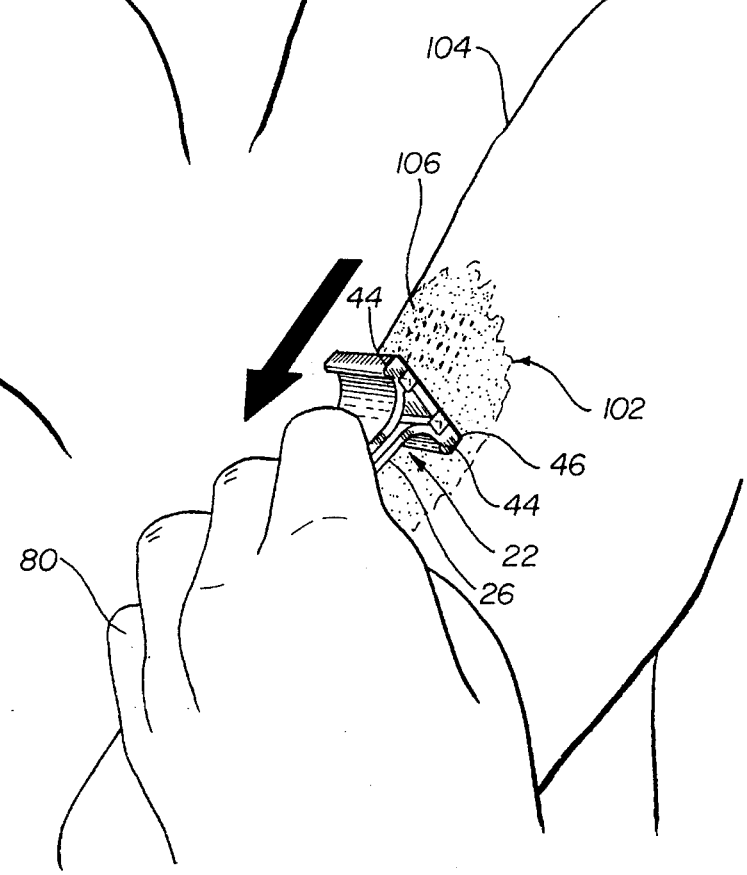
FIG. 6 is a partial fragmentary view of the patient's arm and inoculation site as shown in FIG. 5 after being punctured by the vaccine applicator and whereupon a wiping edge of the vaccine applicator is used to spread the vaccine material over the punctured surface and into the puncture holes.

The applicator system 20 further prevents contact with the spiked portion 28 by way of the guard sections 44 and the outwardly stepped wall 54. When a user grasps the grip portion 40 of the handle 26 as shown in FIG. 1, the guard sections 44 prevent a user's hand 80 from extending over the outside edges 72 of the handle 26. The outwardly and upwardly extending structure of the guard sections 44 provide a barrier between the grip 40 and the wiping edge 46 when the applicator 22 is used to redistribute vaccine material (see FIG. 6). The stepped walls 54 allow a user's hand to enter the cavity 58 but shield the user from contact with the spiked portion 28.

As an additional protective measure, the base panel 56 has a thickness dimension 82 which is thicker than a thickness dimension 84 of the walls 54. The increased thickness dimension 82 provides a further barrier between breaching the sterile environment inside the container 52 and possible puncture and contamination by the spikes 29. Additionally, the height dimension 86 measure between a top surface 76 of the ledge 66 and an inside surface 88 of the base panel 56 is greater than the length dimension 90 of the spike 29. The difference between the height dimension 86 and the length dimension 90 defines a gap 92 between the tip 31 of the spike 29 and the inside surface 88 of the base panel 56. The gap 92 provides a margin of safety to further prevent the spikes 29 from puncturing the base panel 56.

In use, the applicator system 20 is made by attaching the spiked portion 28 to the handle 26. Attachment of the spiked portion 28 is simplified by the attachment means 30 such that the attachment is a press fit assembly. The packaging assembly 24 is formed by forming a plastic material, by vacuum forming or any other acceptable method, to form the container 52 having the walls 54 and the base panel 56. The container 52 is formed with a flange 94 which provides further protection between the user's hand 80 and the spiked portion 28 when removing the applicator from and inserting the applicator into the container 52. The flange 94 also provides a surface for attachment of a sealing cover 96 over a mouth 97 of the container 52.

The assembly is maintained in a sterile condition as a result of the applicator 22 being retained in the cavity 58 with the cover 96 sealed to the container 52. The cover may be provided in the form of a microporous material which will allow for gas sterilization. Another method of sterilizing the applicator assembly 20 is by way of gamma radiation. By using a gamma radiation sterilization system, the applicator 22 can be packaged in the packaging assembly 24 and then sterilized. This method of sterilization eliminates the step of maintaining a sterile assembly environment.

Sterility of the applicator assembly 20 is maintained indefinitely as long as the cover 96 is not removed from the container 52. As discussed hereinabove, the structure of the container 52 and the applicator 22 prevent the spikes 29 from puncturing the container 52 during storage and prior to use.

The ribs 70 engage the base 42 to prevent movement of the applicator 22 in the container 52. The dimensional differences between the height 86 of the ledge 66 and the length 90 of the spikes 29, resulting in the gap 92, further prevent breach of the sterile environment in the sealed cavity 58.

When a technician uses the applicator system 20, the user grasps an outside surface 98 of the container 52 and peels the cover 96 away from the flange 94. The technician next reaches inside the cavity to grasp the grip 40 of the handle 26. Firmly holding the grip 40, the technician then twists or tilts (see FIG. 7, reference arrow 100) to dislodge one edge 72 of the base 42 from engagement between the rib 70 and the ledge 66. Having disengaged one edge 72 the other edge will more easily disengage from the opposite rib and ledge 70, 66. While disengaging the applicator 22 from the container 52, the user's hands are protected by the stepped construction of the walls 54 and the flange 94.

Next, the user extracts the applicator 22 from the cavity 58 and places the packaging assembly 24 aside for later use and disposing of the contaminated applicator 20 view. The applicator 22 is positioned over an inoculation site 102 on a patient's arm 104 which has been swabbed with a vaccine preparation prior to removing the applicator 22 from the packaging assembly 24. The tips 31 of the spikes 29 are positioned against the patient's arm and forcibly driven into the patient's arm by applying pressure to the handle 26. The spikes 29 puncture the patient's skin thereby driving vaccine through the skin and into the puncture holes created by the spikes 29. The technician may then rock the applicator base 42 in order to assure complete puncturing by each of the spikes.

Continuing, the technician removes the applicator 22 from the patient's arm and then maneuvers the applicator to position the wiping edge 46 in the vaccination site 102 to redistribute vaccine over a puncture hole pattern 106 left by the spikes. Redistribution of the vaccine into the puncture holes of the pattern 106 forces additional vaccine into the holes to assure thorough vaccination.

Throughout the operations as shown in FIGS. 1, 5 and 6, the user's hand is prevented from slipping or moving off of the grip 40 by the guard sections 44. Additionally, the guard sections 44 prevent contact between the technician and the inoculation site 102. During the vaccination process, the technician does not need to touch the spiked portion 28 and is protected from contacting the vaccine preparation as well as any fluid such as blood which may well up in the puncture pattern 106. The vaccine preparation and body fluids which contact, and thereby contaminate, the applicator 22 are spaced away from the grip 40 reducing the risk of contaminating the technician. Additionally, the packaging assembly 24 reduces the risk of contaminating the applicator 22 before use and therefore reduces the risk of contaminating or infecting the patient during the vaccination process. Further still, by guarding the technician's hands against contact with the spiked portion 28, the patient is further protected from being contaminated or infected by the technician.

After completing the vaccination steps as shown in FIGS. 5 and 6, the applicator 22 is returned to the packaging assembly 24 for disposal. The applicator 22 is maneuvered into the cavity 58 at a slight angle or tilt (100) so that one side 72 of the base 42 is engaged between the rib 70 and the ledge 66. Once the side 72 is positioned and captured between the rib and ledge 70, 66, the grip 40 is tilted to snap engage the opposite side between the corresponding rib and ledge 70, 66. As an additional matter, the inward spacing of the spikes 29 away from the lower wall 68 prevents the spikes 29 from puncturing the lower wall 68 during the removal and replacement operations.

Any vaccine or blood which may have accumulated on the spiked portion 28 of the applicator 22 will collect in the inside surface 88 of the base panel 56. The engagement between the edges 72 and the rib and ledge 70, 66 provide an isolation barrier to prevent contact with any contaminates in the container 52.

The entire applicator system 20 is easily produced at a low cost making it cost effective to dispose of each applicator 22 and packaging assembly 24 after a single use. In contrast, prior art devices reused a magnetic handle portion for numerous vaccination procedures. Further, the packaging assembly 24 reduces the risk of contamination prior to and after use since the technician is shielded or guarded from contact with the spiked portion throughout the vaccination procedure. In contrast, prior art devices require the technician to handle the spiked portion as a separate component thereby exposing a technician to risk of contamination.

While a preferred embodiment of the present invention is shown and described, it is envisioned that those skilled in the art may devise various modifications of the present invention without departing from the spirit and scope of the appended claims. The invention is not intended to be limited by the foregoing disclosure.

The invention claimed is:

1. In a percutaneous vaccine applicator system, a packaging assembly for use with a percutaneous vaccine applicator of the type having a plurality of spikes, said packaging assembly providing for applicator storage and disposal, said packaging assembly comprising:

a container and a removable cover attached to said container, said container having walls and a base panel defining a container cavity, said container cavity being sized and dimensioned for receiving a percutaneous vaccine applicator, a ledge formed in said walls, a ledge rim surface of said ledge being spaced away from an inside surface of said base panel a dimension which is greater than the length of the spikes on a percutaneous vaccine applicator to be retained in said container cavity for maintaining a gap between a tip of the spikes of the applicator and an inside surface of said base panel to prevent the spikes from puncturing said base panel, at least one detent protrusion projecting into said cavity from a corresponding wall, said detent protrusion being spaced from a corresponding portion of said ledge rim to retain a portion of said applicator therebetween prior to use and for disposal after use.

2. In a percutaneous vaccine applicator system as recited in claim 1, said packaging assembly further comprising, said base panel having a thickness dimension which is greater than the thickness dimension of the walls, said base panel having sufficient thickness to resist puncture by the spikes on the applicator.

3. In a percutaneous vaccine applicator system as recited in claim 1, said packaging assembly further comprising a flange extending outwardly from said mouth, said flange providing a shield to prevent accidental contact with said spikes, and a surface for the attachment of said cover over said mouth.

4. A percutaneous vaccine applicator system, said system comprising: a percutaneous vaccine applicator including a handle having a base, and a spiked portion attached to said base for puncturing the skin of a patient; a packaging assembly including a container and a removable cover attached to said container, said container having inwardly stepped walls and a base panel defining a hollow cavity, said stepped walls defining at least one ledge being spaced away form an inside surface of said base panel a dimension which is greater than the length of said spikes on said applicator retained in said container, a portion of said face of said base abutting said ledge, said ledge maintaining a gap between a tip of said spikes for preventing said spikes from puncturing said base panel of said container, at least one detent protrusion positioned on an inside surface of said wall spaced away from a corresponding portion of said ledge, a portion of said base being captured between said detent protrusion and said ledge for positively retaining said applicator in said cavity.

5. A percutaneous vaccine applicator system as recited in claim 4, wherein said base panel has a thickness dimension which is greater than the thickness dimension of the walls, said base panel having sufficient thickness to resist puncture by said spikes on said applicator.

6. A packaging assembly for use with a vaccine applicator of the type having a handle, a base attached to said handle and a plurality of spikes extending form said base, said packaging assembly providing for applicator storage and disposal, said packaging assembly comprising:

a container having at least one wall and a base portion extending therebetween defining a container cavity, an edge of said wall opposite said base portion defining a mouth of said container, and a removable cover attached generally over said mouth for closing said container cavity being sized and dimensioned for receiving a vaccine applicator, at least one detent protrusion positioned on an inside surface of said wall projecting into said cavity for positively retaining said applicator in said cavity prior to use, said detent protrusion being deflectable for allowing removal of said applicator and to receive said applicator after use, said detent protrusion retaining said applicator in said cavity for disposal.

7. A packaging assembly as recited in claim 6, said packaging assembly having inwardly stepped walls, said stepped walls defining at least one ledge being spaced away from an inside surface of said base panel a dimension which is greater than the length of said spikes on said applicator retained in said container, a portion of said base abutting said ledge, said ledge maintaining a gap between a tip of said spikes for preventing said spikes from puncturing said base panel of said container.

8. A packaging assembly as recited in claim 7, further comprising at least one elongated detent protrusion positioned on an inside surface of said wall spaced away from a corresponding portion of said ledge, an elongated portion of said base being captured between said elongated detent protrusion and said ledge for positively retaining said applicator in said cavity.

9. A packaging assembly as recited in claim 6, said packaging assembly further comprising, said base panel having a thickness dimension which is greater than the thickness dimension of said wall, said base panel having sufficient thickness to resist puncture by said spikes on said applicator.

10. A packaging assembly as recited in claim 6, said packaging assembly further comprising a flange extending outwardly from said mouth, said flange providing a shield to prevent accidental contact with said spikes, and a surface for the attachment of said cover over said mouth.

* * * * *